United States Patent [19]

Sakai et al.

[11] Patent Number: 5,528,225
[45] Date of Patent: Jun. 18, 1996

[54] GAS DETECTING METHOD AND APPARATUS

[75] Inventors: Sai Sakai; Mikiya Nakatani, both of Osaka, Japan

[73] Assignee: New Cosmos Electric Co., Ltd., Osaka, Japan

[21] Appl. No.: 328,085

[22] Filed: Oct. 24, 1994

[30] Foreign Application Priority Data

Nov. 8, 1993 [JP] Japan ................................. 5-277964
Aug. 3, 1994 [JP] Japan ................................. 6-182168

[51] Int. Cl.$^6$ ................................. G08B 17/10
[52] U.S. Cl. .................. 340/632; 340/634; 422/90; 422/94; 422/98
[58] Field of Search .................. 340/632, 634; 422/94, 95, 98, 90, 97; 338/34, 35; 73/31.05, 31.06

[56] References Cited

U.S. PATENT DOCUMENTS

| | | | |
|---|---|---|---|
| 4,535,315 | 8/1985 | Sakai | 338/34 |
| 4,567,475 | 1/1986 | Bukowiecki et al. | 340/634 |
| 4,592,967 | 6/1986 | Komatsu et al. | 428/697 |
| 5,019,885 | 5/1991 | Yagawara et al. | 357/25 |
| 5,061,447 | 10/1991 | Ono | 422/96 |

FOREIGN PATENT DOCUMENTS

| | | |
|---|---|---|
| 0115953 | 8/1984 | European Pat. Off. . |
| 0444753 | 9/1991 | European Pat. Off. . |
| 1479925 | 7/1977 | United Kingdom . |
| WO91/06849 | 5/1991 | WIPO . |

OTHER PUBLICATIONS

Patent Abstracts of Japan, JP 1221649, Sep. 5, 1989, Nakamura Yuji, Detection of Gaseous Carbon Monoxide and Sensor Used Therefor as Well as Detection of Carbon Monoxide and Gaseous Methane and Sensor Used Therefor.
Patent Abstracts of Japan, JP62015449, Jan. 23, 1987, Tsurumi Shigeyuki, Micro Gas Sensor.
Patent Abstracts of Japan, JP 4147048, May 20, 1992, Kimura Toshiyuki, Gas Detection Device.
Patent abstracts of Japan, JP61070448, Apr. 11, 1986, Nobetani Toru, Gas Detecting Element.

*Primary Examiner*—Brent A. Swarthout
*Assistant Examiner*—Julie B. Lieu
*Attorney, Agent, or Firm*—Jones, Tullar & Cooper

[57] ABSTRACT

A gas detecting method and apparatus for selectively detecting a fuel gas having methane as a main component thereof and an incomplete combustion gas having carbon monoxide as a main component thereof. A low heat capacity, hot-wire semiconductor type gas sensor used has an oxide semiconductor formed mainly of valency-controlled tin oxide and acting as a sensitive section thereof. An inactive to gas combustion, heat resistant, quadrivalent metallic oxide is mixed into the sensitive section. The sensitive section is alternately switched between a fuel gas detecting temperature and an incomplete combustion gas detecting temperature.

11 Claims, 12 Drawing Sheets

GAS DETECTING METHOD AND APPARATUS

BACKGROUND OF THE INVENTION

1. Field Of The Invention

This invention relates to a gas detecting method and apparatus. More particularly, the invention relates to a method of selectively detecting a fuel gas having methane as a main component thereof and an incomplete combustion gas having carbon monoxide as a main component thereof, and to a gas detecting apparatus for use in executing this method. The invention employs a low heat capacity, hot-wire semiconductor type gas sensor having an oxide semiconductor formed mainly of tin oxide and acting as a sensitive section thereof.

2. Description Of The Related Art

Conventional semiconductor gas sensors for selectively detecting different types of gases as noted above are disclosed in Japanese Utility Model Publication No. 1993-32760 and Japanese Patent Publication Kokai No. 1992-147048.

The gas sensor disclosed in the former publication is intended to detect carbon monoxide as incomplete combustion gas, and methane, butane and the like as fuel gas. This sensor detects the incomplete combustion gas at a relatively low temperature in the order of 80° C., and the fuel gas at a high temperature in the order of 400° C. The sensor includes a sensitive section formed of an oxide semiconductor having tin oxide as a main component thereof. The sensitive section has a sensitizer such as palladium added thereto to increase its sensitivity. The fuel gas may be detected in a relatively short time (20 to 30 sec.), but a relatively long time of at least 90 sec. is required for detecting carbon monoxide.

The gas sensor disclosed in the latter publication is similar to that disclosed in the former publication in its object of detecting gases. The latter has relatively high temperature ranges of detection (the sensitive section becoming 300° C. when detecting an incomplete combustion gas, and 500 to 600° C. when detecting a fuel gas). The sensitive section of this sensor is formed of a metallic oxide semiconductor having tin oxide as a main component thereof, with a trace of platinum added thereto to adjust its sensitivity.

This sensitive section has a small outside diameter not exceeding 1 mm, and the sensor itself has a relatively low heat capacity, to realize a shortened response time.

However, the conventional sensors noted above have the following drawbacks.

The gas sensor disclosed in Japanese Utility Model Publication No. 1993-32760 has a peak of sensitivity to carbon monoxide at a temperature below 90° C. This gas sensor has selectivity for a fuel gas only in a low temperature range of 40 to 80° C.

In such a temperature range, therefore, some time is required for the sensor to adsorb carbon monoxide and reach equilibrium. The sensor has a poor response performance with a slow output response, taking 90 seconds to effect a reproducible detection of a CO concentration. Carbon monoxide is a highly dangerous gas, its permissible concentration (threshold limit value) being at 50 ppm. It is therefore desirable to detect leakage within a shorter time.

Where the oxide semiconductor has a precious metal such as palladium or platinum to act as a sensitizer, carbon monoxide which is flammable, usually, is partially burned at 100° C. or above, instead of reaching the sensor interior. Consequently, the sensor inevitably has a low sensitivity to carbon monoxide.

With the gas sensor disclosed in Japanese Patent Publication Kokai No. 1992-147048, on the other hand, responsivity is secured by its low heat capacity (which actually is achieved by the small diameter sensitive section thereof) and the like. However, the sensitivity characteristics shown in FIG. 3 of this prior publication are data obtained from the respective gases at a high concentration of 4,000 ppm. The sensitivity to carbon monoxide remains low. As seen from FIG. 4 of the publication, the selectivity for carbon monoxide is also low. That is, no selection can be made between carbon monoxide and methane around 500 ppm. It is impossible to determine with sufficient certainty whether detection is made of a gas resulting from incomplete combustion or a leakage of methane or the like used as fuel. Regarding concentration dependence, this gas sensor has a disadvantage of easily becoming saturated at a low concentration. Further, this gas sensor cannot be said to have sufficiently high sensitivity characteristics with respect to carbon monoxide. Since a fuel gas is detected at a high temperature range of 500 to 600° C., particles constituting the oxide semiconductor tend to be sintered quickly, resulting in a short sensor life. To summarize the above facts, this sensor provides, at low temperatures, signals representing miscellaneous gases such as of hydrogen, carbon monoxide and alcohol, thereby to perform a function in the nature of air monitoring. The gas sensor has low measurement reproducibility and reliability as a carbon monoxide concentration measurement and alarm device for preventing incomplete combustion poisoning. The sensor cannot be said to be reliable for detecting and discriminating between gases generated through incomplete combustion and a fuel gas.

SUMMARY OF THE INVENTION

Having regard to the drawbacks of the prior art noted above, the object of the present invention is to provide a gas detecting method and apparatus having high measurement reproducibility and reliably, which is capable of promptly detecting and discriminating between gases generated through incomplete combustion and leaks or the like of a fuel gas, and reliably measuring carbon monoxide concentrations to prevent incomplete combustion poisoning.

The above object is fulfilled, according to the present invention, by a gas detecting method comprising the step of selectively detecting a fuel gas having methane as a main component thereof and an incomplete combustion gas having carbon monoxide as a main component thereof, with a low heat capacity, hot-wire type semiconductor gas sensor having an oxide semiconductor formed mainly of tin oxide ($SnO_2$) and acting as a sensitive section thereof, wherein an inactive to gas combustion, heat resistant, quadrivalent metallic oxide is mixed into the sensitive section which is formed mainly of valency-controlled tin oxide, the hot-wire semiconductor type gas sensor includes a dense sintered layer formed on a surface of the sensitive section by sintering tin oxide having a large specific surface area, the sensitive section is alternately switched between a fuel gas detecting temperature and an incomplete combustion gas detecting temperature, the fuel gas is detected at the fuel gas detecting temperature, and the incomplete combustion gas is detected at the incomplete combustion gas detecting temperature.

In a further aspect of the invention, there is provided a gas detecting apparatus comprising a sensitive section including a low heat capacity, hot-wire semiconductor type gas sensor having an oxide semiconductor formed mainly of tin oxide, the sensitive section selectively detecting a fuel gas having methane as a main component thereof and an incomplete combustion gas having carbon monoxide as a main component thereof, wherein the hot-wire type semiconductor gas sensor includes the sensitive section having valency-controlled tin oxide as a main component thereof, with an inactive to gas combustion, heat resistant, quadrivalent metallic oxide mixed into the sensitive section, and a dense sintered layer of large specific surface area formed on a surface of the sensitive section, the apparatus further comprising a switching device for alternately switching the sensitive section between a fuel gas detecting temperature and an incomplete combustion gas detecting temperature.

Functions of the gas detecting method and apparatus according to the present invention will be described in comparison with the characteristics of the sensor disclosed in Japanese Patent Publication 1992-147048 (hereinafter referred to as the conventional sensor).

The differences in function between the sensor according to the present invention and the conventional sensor are tabulated below.

|  | sensor of the invention | conventional sensor |
| --- | --- | --- |
| additive to oxide semiconductor | quadrivalent metallic oxide (to inhibit activity) | precious metal catalyst (to act as sensitizer) |
| dense surface layer | present | absent |
| temp. of sensitive section | actively switched | passively switched |

As noted above, the sensor according to the present invention differs from the conventional sensor in the substance mixed into the oxide semiconductor, the formation of the dense surface layer, and the active temperature switching of the sensitive section. The sensitive section of the sensor according to the present invention has a quadrivalent metallic oxide instead of a precious metal sensitizer. Further, the dense surface layer provides the sensor according to the present invention with appropriate activity. That is, the sensor according to the present invention has a lowered temperature range of maximum sensitivity to methane which is a main component of a fuel gas.

On the other hand, carbon monoxide is inhibited from burning at the surface of the sensitive section at 200 to 300° C., to reach the vicinity of a detecting electrode inside the sensor with facility, thereby increasing the sensitivity to carbon monoxide in this temperature range. By positively switching the temperature of the sensitive section, the range of maximum sensitivity to carbon monoxide is shifted to a lower temperature range to increase sensitivity. By repeatedly switching the sensitive section between high a temperature and a low temperature, long-term stability is secured for detection in the low temperature range.

This aspect will be described with reference to FIGS. 6 through 8. The description will be made, taking ceria for example which is a typical inactive to gas combustion, heat resistant, quadrivalent metallic oxide.

These figures show variations of sensitivity characteristics with respect to methane (in solid lines), carbon monoxide (in broken lines) and alcohol (in two-dots-and-dash lines). The vertical axis represents sensitivity or outputs, while the horizontal axis represents surface temperatures of the sensitive section. In these figures, the circles show the sensitivity characteristics occurring when the sensor according to the present invention is continuously maintained at a fixed temperature (noted "continuous electrification" in the figures), the black dots show the sensitivity characteristics occurring when the sensor according to the present invention is continually switched between the two different temperatures (noted "Hi/Lo" in the figures), and the crosses show the sensitivity characteristics of the conventional sensor occurring when used in continuous detection (with the sensor temperature passively varied by a correlation between sensor resistance and load resistance).

Each figure will be described hereinafter.

As seen from FIG. 6, compared with the conventional sensor, the sensor according to the present invention has a sensitive temperature range lowered from around 600° C. to around 400° C. The detecting temperature switching provides increased sensitivity to methane in a low temperature range.

Regarding the sensitivity to carbon monoxide, as shown in FIG. 7, the sensor according to the present invention is more sensitive than the conventional sensor. The detecting temperature switching produces the effect of lowering the temperature range of maximum sensitivity to this gas, to thereby increasing sensitivity significantly. Regarding the sensitivity to alcohol, as shown in FIG. 8, the sensor according to the present invention has the range of maximum sensitivity shifted to a low temperature, compared with the conventional sensor. The detecting temperature switching provides a slightly increased sensitivity to this gas.

To summarize the results described above, the carbon monoxide detecting temperature is raised by adding to the tin oxide semiconductor an inhibitor rather than the sensitizer used in the prior art. The temperature showing the maximum sensitivity to the fuel gas is lowered by forming an active, dense sintered layer having a large specific surface area on the surface of the sensitive section. A sufficiently high selectivity for discriminating between the two gases is achieved by switching the detecting temperature between high and low, as described later with reference to FIGS. 3 through 5. Further, the sensor according to the present invention itself has a low heat capacity, to thereby exhibit excellent responsivity.

Preferably, the sensitive section has an outside diameter of 1 mm at most; the inactive to gas combustion, heat resistant, quadrivalent metallic oxide is at least one of a metallic oxide selected from ceria ($CeO_2$), silicon oxide ($SiO_2$), titanium oxide ($TiO_2$) and zirconium oxide ($ZrO_2$); the metallic oxide is mixed in a ratio of 0.01 to 0.5,mol % with respect to the tin oxide; and the dense sintered layer is formed in a thickness of 1 to 20 μm on a surface of the sensitive section by sintering tin oxide having a specific surface area of 50 to 150 $m^2/g$.

The size of the sensitive section, the oxide mixed, its mixing ratio, and the thickness and specific surface area of the dense sintered layer are specified as above. With the sensitive section having an outside diameter not exceeding 1 mm, the temperature of the sensitive section stabilizes in about 2 seconds in time of Hi/Lo switching. By employing any one of the particular metallic oxides noted above, as shown in FIG. 12, a higher sensitivity to carbon monoxide is secured than where different metallic oxides are mixed. Consequently, the sensor has improved selectivity with respect to other gases also. As shown in FIG. 12, a preferred mixing ratio is 0.01 to 0.5 mol% to achieve high sensitivity. A mixing ratio of 0.03 to 0.3 mol% is particularly preferred, which provides optimal sensitivity.

Regarding the thickness and specific surface area of the dense sintered layer, a surface thickness less than 1 btm or a specific surface area less than 50 m²/g would provide insufficient methane selectivity in a high temperature range. A surface thickness exceeding 20 μm or a specific surface area larger than 150 m²/g would impair selectivity to carbon monoxide in a low temperature range.

Preferably, the switching device of the hot-wire semiconductor type gas sensor comprises an applied voltage switching device for switching voltages applied to the semiconductor gas sensor.

For temperature control of this type of sensor, voltage control is easy and allows a simple construction to fulfill the intended object.

Preferably, the fuel gas detecting temperature is around 450° C., and the incomplete combustion gas detecting temperature is around 300° C., the alternate switching between the fuel gas detecting temperature and the incomplete combustion gas detecting temperature being effected every unit time.

The switching device may effect the alternate switching between the fuel gas detecting temperature and the incomplete combustion gas detecting temperature every unit time.

With this construction, the sensor detects, in a lower temperature range, the incomplete combustion gas having carbon monoxide as a main component thereof and, in a higher temperature range, the fuel gas having methane as a main component thereof. Where the detecting temperatures are alternately switched every fixed unit of time, the respective gases may be detected in equal conditions, and a control system may be simplified.

Preferably, an activated carbon filter is disposed in an area of gas passage leading to the sensitive section.

Then, no detection will be made of a high concentration (in the order of 2,000 ppm) of alcohol produced by cooking, for example. This provides the effect of avoiding a false alarm.

Thus, the present invention provides a gas detecting method and apparatus having high measurement reproducibility and reliability, which is capable of promptly detecting and discriminating between gases generated through incomplete combustion and leaks or the like of a fuel gas, and reliably measuring and giving an alarm of carbon monoxide concentrations to prevent incomplete combustion poisoning.

The invention described in Japanese Utility Model Publication No. 1993-32760 has a serious drawback in responsivity since carbon monoxide is detected at 40 to 80° C. (i.e. below 100° C.). The present invention detects carbon monoxide at a higher temperature than in the prior invention. Thus, an equilibrium of gas adsorption and desorption is attained quickly. This, combined with the reduced size, increases response speed in repeated switching between high temperature and low temperature. The present invention is capable of carbon monoxide detection in a highly practical manner.

Other features and advantages of the present invention will be apparent from the following description.

DETAILED DESCRIPTION OF THE PREFERRED EMBODIMENTS

Embodiments of the present invention will be described in detail with reference to the drawings.

The illustrated gas detecting apparatus is used for selectively detecting a fuel gas having methane as a main component thereof, and an incomplete combustion gas having carbon monoxide as a main component thereof (possibly hydrogen gas as well).

Figure 1A:
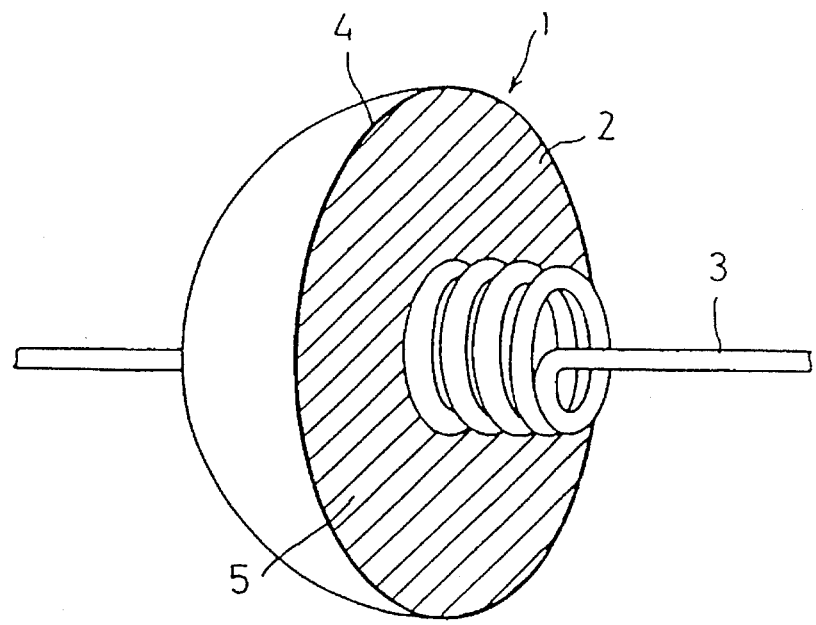
FIG. 1(a) and FIG. 1(b) are views showing a hot-wire semiconductor type gas sensor and a detection system according to the present invention.

FIG. 1(a) shows a construction of what is known as a hot-wire semiconductor type gas sensor 1 employed in the gas detecting apparatus of the present invention. This semiconductor gas sensor 1 includes a sensitive section 2 which is an oxide semiconductor formed mainly of tin oxide, and a coil resistor 3 mounted in the sensitive section 2 and formed of platinum or other precious metal (which may be an alloy thereof). The gas sensor 1 detects gases present adjacent the sensitive section 2 based on variations in the combined resistance of the coil resistor 3 and the oxide semiconductor. In manufacture, the oxide semiconductor is applied to and sintered on the coil resistor 3. In use, this hot-wire semiconductor type gas sensor 1 is incorporated into a Wheatstone bridge as one of the resistors thereof (FIG. 1(b)), to detect gases based on variations in combined resistance.

A hot-wire semiconductor type gas sensor 1 carrying ceria ($CeO_2$) and a detection system 10 will be described hereinafter.

The semiconductor gas sensor 1 includes a sensitive section 2 which is an oxide semiconductor formed mainly of valency-controlled tin oxide. A dense sintered layer 4 is formed on a surface of the sensitive section 2 by sintering tin oxide having a large specific surface area. The sensitive section 2 is minimized to 1 mm ϕ or less. With the minimized sensitive section 2, a sintered body has a reduced thickness from the surface of sensitive section 2 to the coil resistor 3 acting as a detection electrode. Consequently, carbon monoxide is burned at a reduced rate, thereby realizing improved sensitivity at a low temperature range (around 300° C.). Further, the sensor 1, because of the minimized size, reaches a thermal equilibrium quickly in time of temperature increase or decrease, and also an adsorption/desorption equilibrium in the low temperature range quickly. Consequently, carbon monoxide is detected within 10 seconds of switching to the low temperature range.

In detecting a fuel gas such as methane in a high temperature range (around 450° C.), the sensor may be thermally controlled with ease, and quickly adsorbs and desorbs the detected gas. This detection may be effected within 5 seconds of switching to the high temperature range.

Ceria ($CeO_2$) is mixed into the tin oxide semiconductor acting as the main component of the sensitive section 2, in a mixing ratio of 0.01 to 0.5 mol % with respect to tin oxide. If ceria were mixed in a ratio less than 0.01 mol %, the sensor would produce an insufficient effect of inhibiting combustion of carbon monoxide. If ceria were mixed in a ratio more than 0.5 mol %, sensor output in the atmosphere would become unstable.

Figure 12:
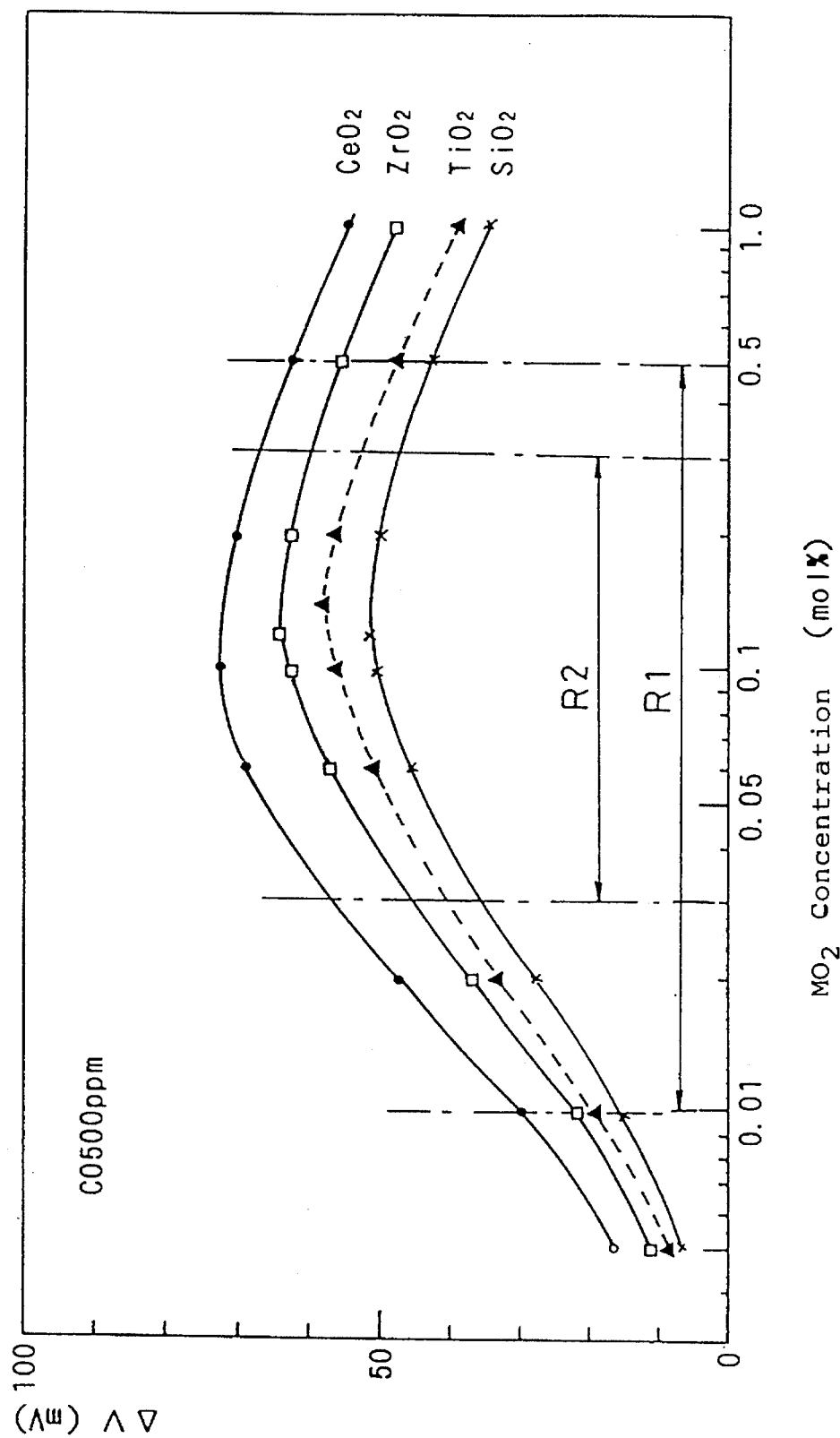
FIG. 12 is a graph showing mixing ratios of the various oxides and variations in maximum sensitivity for CO detection.

FIG. 12 shows a relationship between mixing ratio of ceria ($CeO_2$) with respect to tin oxide ($SnO_2$) and maximum sensitivity for carbon monoxide detection. FIG. 12 also includes results obtained by mixing silicon oxide ($SiO_2$), titanium oxide ($TiO_2$) and zirconium oxide ($ZrO_2$) in accordance with the present invention.

Points of maximum sensitivity in a range of 200° to 300° C. are shown as representing maximum sensitivity to carbon monoxide in an incomplete combustion detecting condition based on Hi/Lo switching. This is because positions of sensitivity peaks in FIG. 3 shift with variations in the mixing ratio.

The results show that a good detection is obtained from the mixing ratio of 0.01 to 0.5 mol % (in range R1 in FIG. 12). A detection with relatively high sensitivity is possible by a mixing ratio of 0.03 to 0.3 mol % (in range R2 in FIG. 12). With any one of the metallic oxides, a mixing ratio in the range of 0.1 to 0.2 mol % shows the highest detection sensitivity optimal to carbon monoxide detection.

The dense sintered layer 4 has a surface thickness in the order of 1 to 20 μm. Tin oxide, before sintering, has a specific surface area of approximately 50 to 150 $m^2/g$. The material forming an interior 5 of the sensitive section 2 has a specific surface area of approximately 10 to 20 $m^2/g$. A surface thickness less than 1 μm or a specific surface area less than 50 $m^2/g$ would provide insufficient methane selectivity in the high temperature range. A surface thickness exceeding 20 μm or a specific surface area larger than 150 $m^2/g$ would impair selectivity to carbon monoxide in the low temperature range.

The gas detecting apparatus includes a switching device (applied voltage switching device) for acting on the hot-wire semiconductor type gas sensor 1. This switching device, by controlling a voltage (current) applied to the coil resistor 3, alternately switches the sensitive section 2 between a fuel gas detecting temperature and an incomplete combustion gas detecting temperature.

Figure 1B:
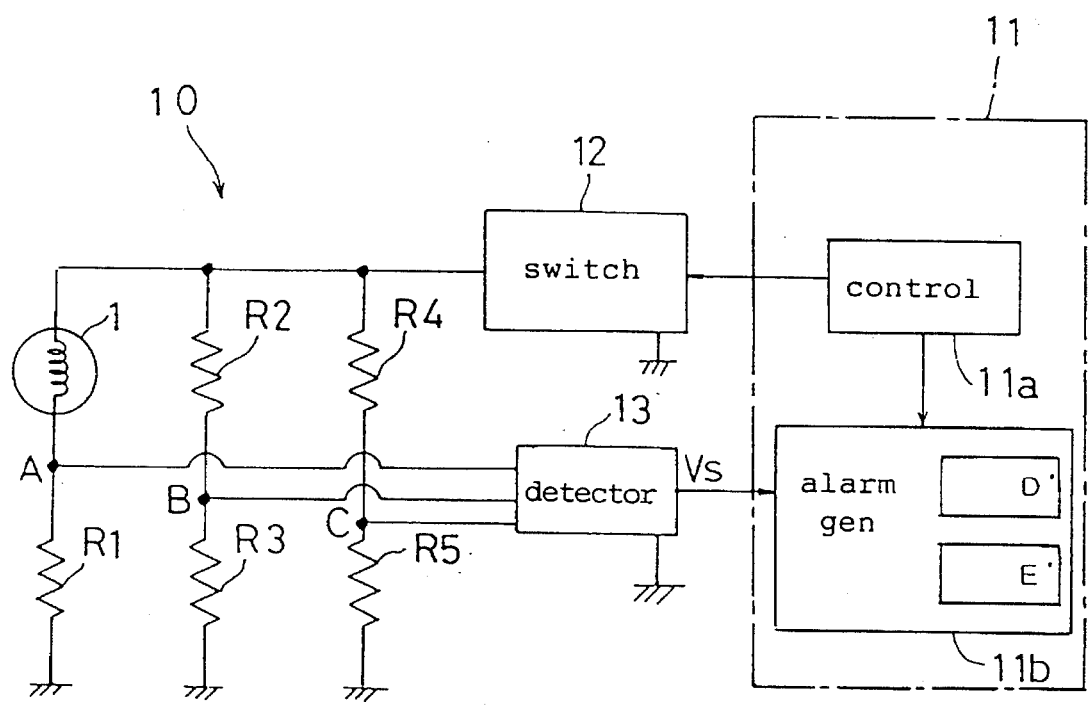

The detection system 10 of the gas detecting apparatus is shown in FIG. 1 (b). This system 10 includes a microcomputer circuit 11 (which has a gas sensor power source controller 11a and a gas sensor alarm generator 11b), a gas sensor Hi/Lo switching power source circuit 12, and a detecting circuit 13. The gas sensor power source controller 11a and gas sensor Hi/Lo switching power some circuit 12 constitute the above-mentioned switching device (applied voltage switching device) to switch voltages applied to the semiconductor gas sensor 1. The system 10 further includes resistors R1–R5 suitably selected according to the gases to be detected. The detecting circuit 13 picks up and determines levels of an output voltage between points A and B when detecting a fuel gas, and an output voltage between points A and C when detecting an incomplete combustion gas. The gas sensor alarm generator 11b gives an alarm as necessary. References D and E in FIG. 1(b) denote alarms relating to the fuel gas and incomplete combustion gas, respectively. The alarms may be given through a light emitter, a visual display such as a liquid crystal display, or a sounding device such as a buzzer.

Next, temperature variations of the sensitive section 2 (shown in FIG. 2(a)) and sensor output conditions (shown in FIG. 2(b)) will be described.

Figure 2A:
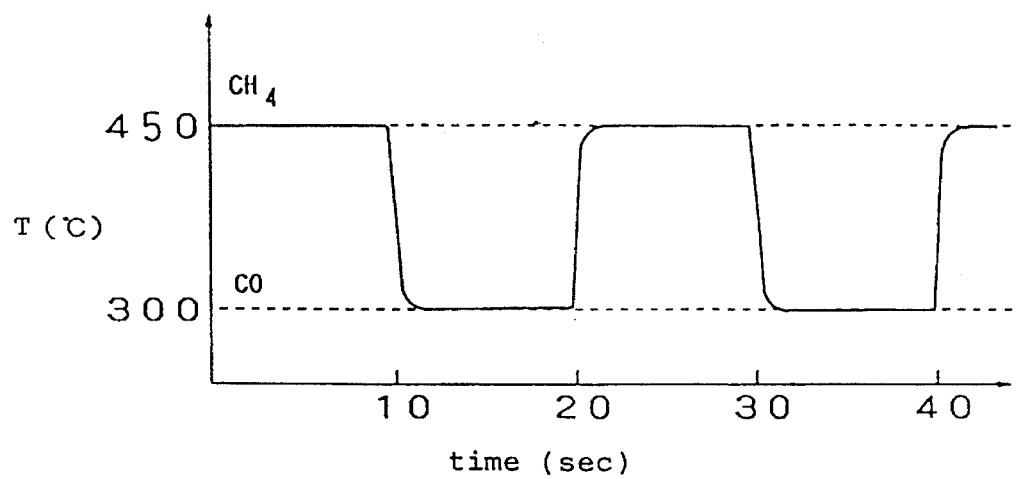
FIG. 2(a) and FIG. 2(b) are time charts showing temperature and sensitivity conditions of a sensitive section of the sensor.

As shown in FIG. 2(a), the temperature of sensitive section 2 is alternately and continually switched every unit time of 10 seconds between 450° C. for detecting the fuel gas and 300° C. for detecting the incomplete combustion gas. Mostly methane is detected at the fuel gas detecting temperature, and carbon monoxide and hydrogen at the incomplete combustion gas detecting temperature.

Figure 2B:
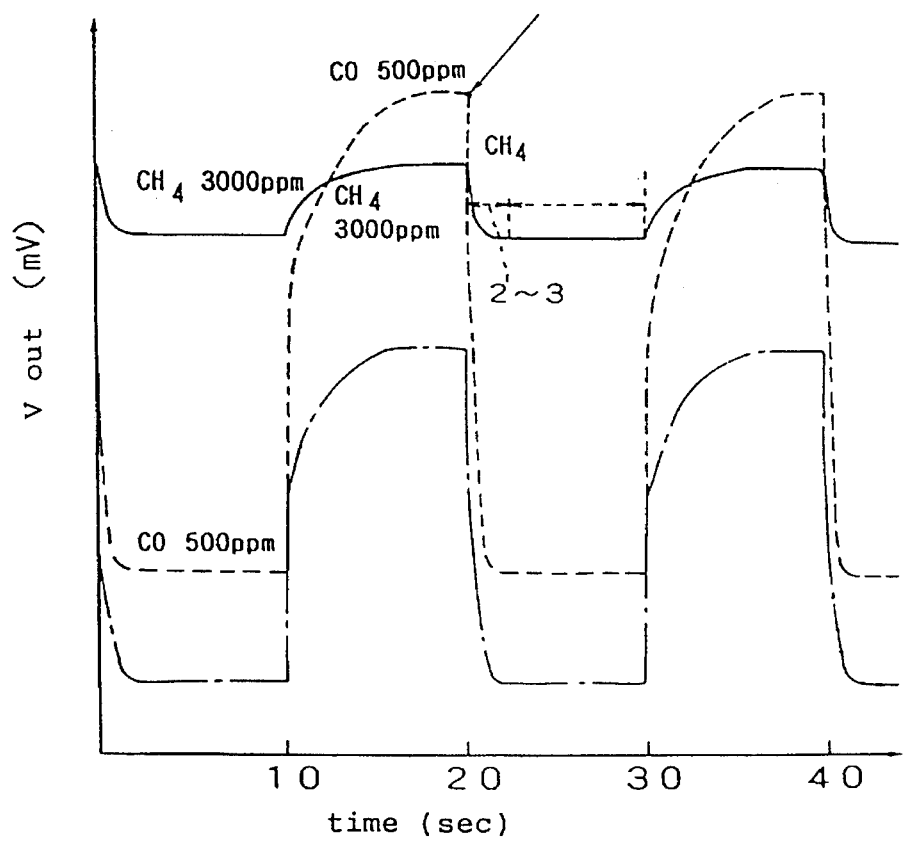

As shown in FIG. 2(b), the fuel gas detection has a gas adsorption equilibrium in transitional state for a few seconds immediately following a switch to the fuel gas detecting voltage. Thus, the gas detection is blinded during this period, and is continued during the remaining period.

In the incomplete combustion gas detection, on the other hand, a gas adsorption equilibrium is reached in about 6 or 7 seconds after a switch to the incomplete combustion gas detecting voltage. Thus, output is detected at the final point of this detecting state (i.e. immediately before a switch to the fuel gas detection). However, reproducibility is excellent even in a transitional state during the first 6 seconds of the incomplete combustion gas detection. Detection may be effected in a short time of about 3 seconds.

In FIG. 2(b), the solid line indicates an output due to methane, the broken line an output due to carbon monoxide, and the dot-and-dash line an output due to air.

Figure 3:
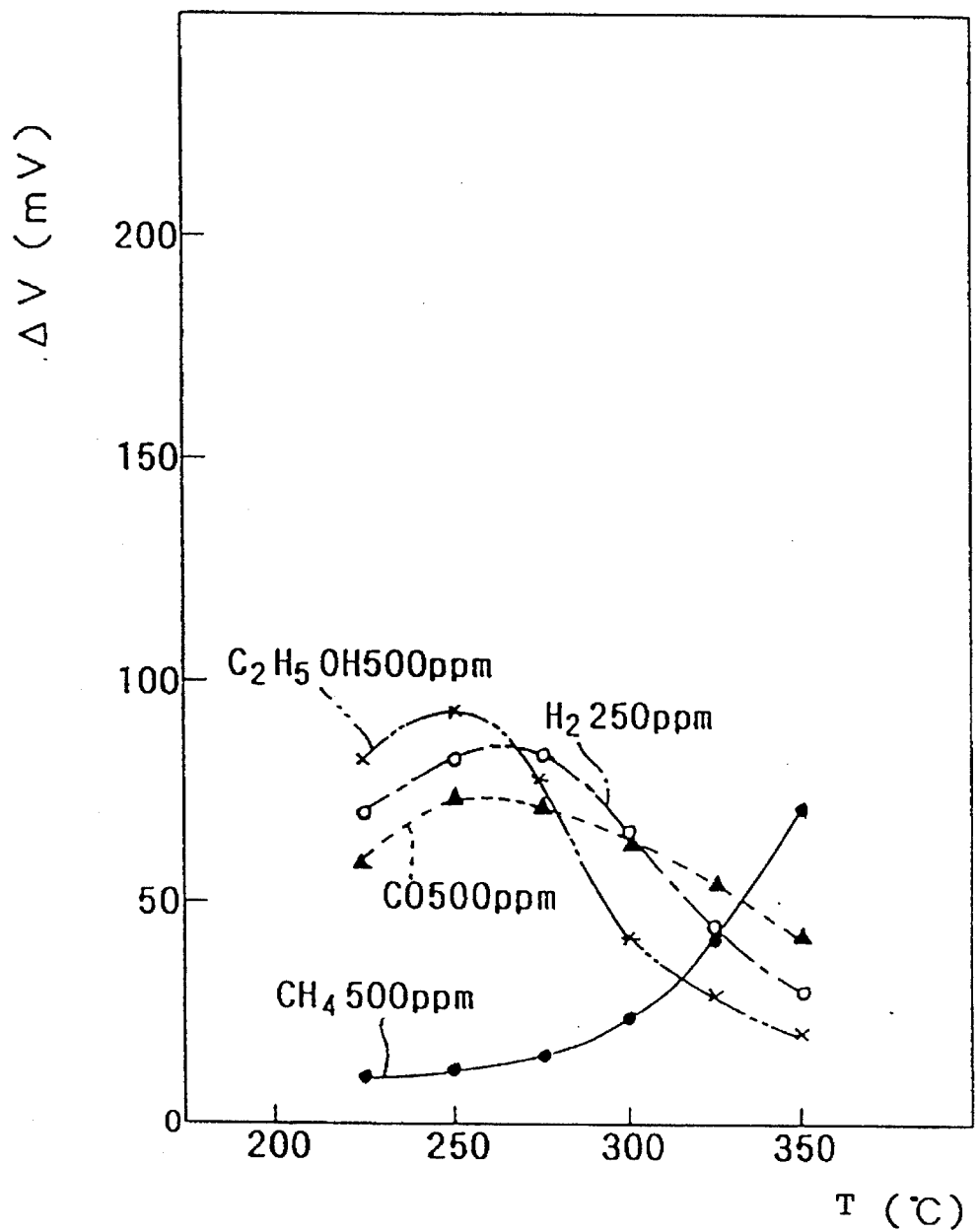
FIG. 3 is a graph showing sensitivity characteristics of the sensor when detecting an incomplete combustion gas.
Figure 4:
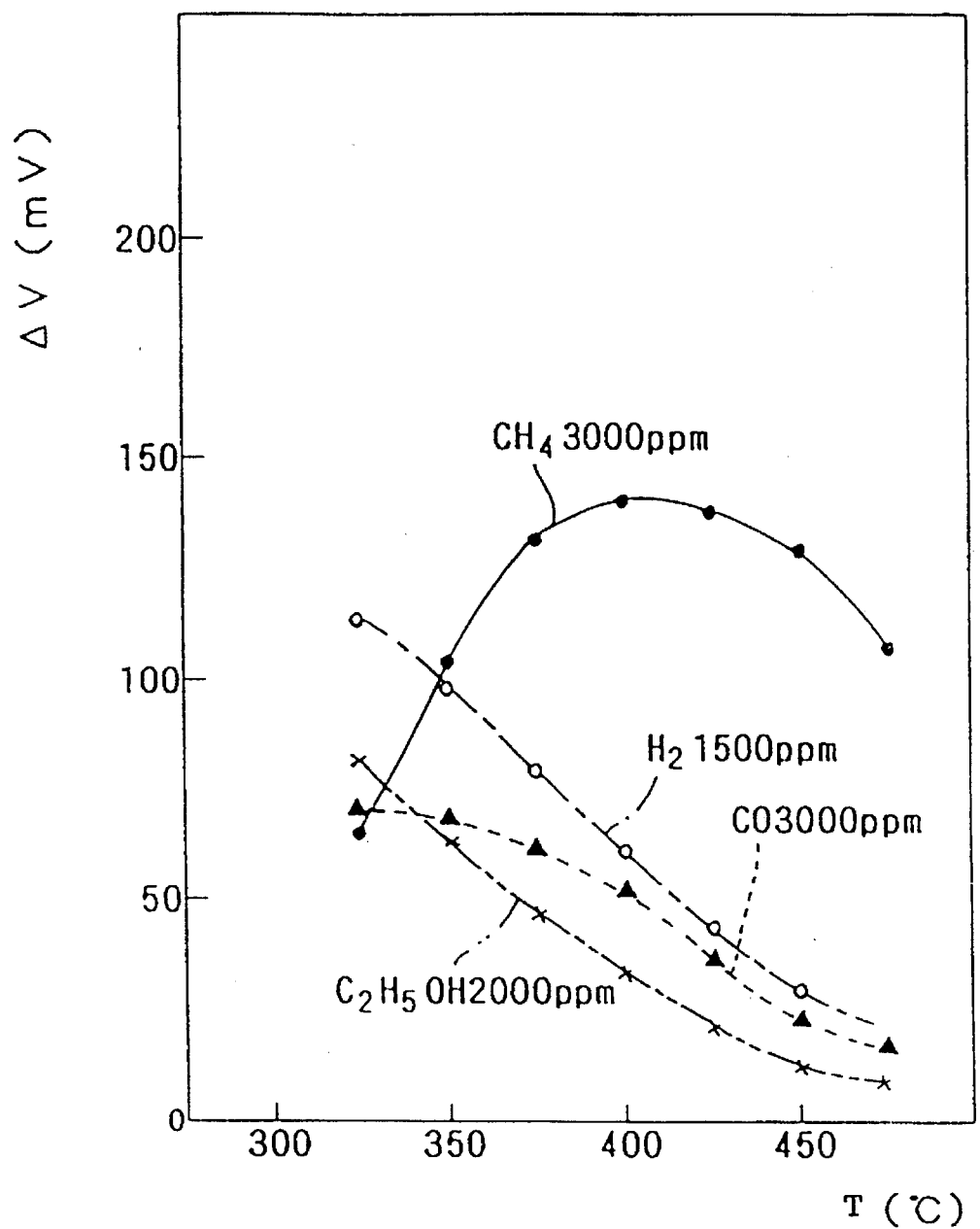
FIG. 4 is a graph showing sensitivity characteristics of the sensor when detecting a fuel gas.
Figure 5:
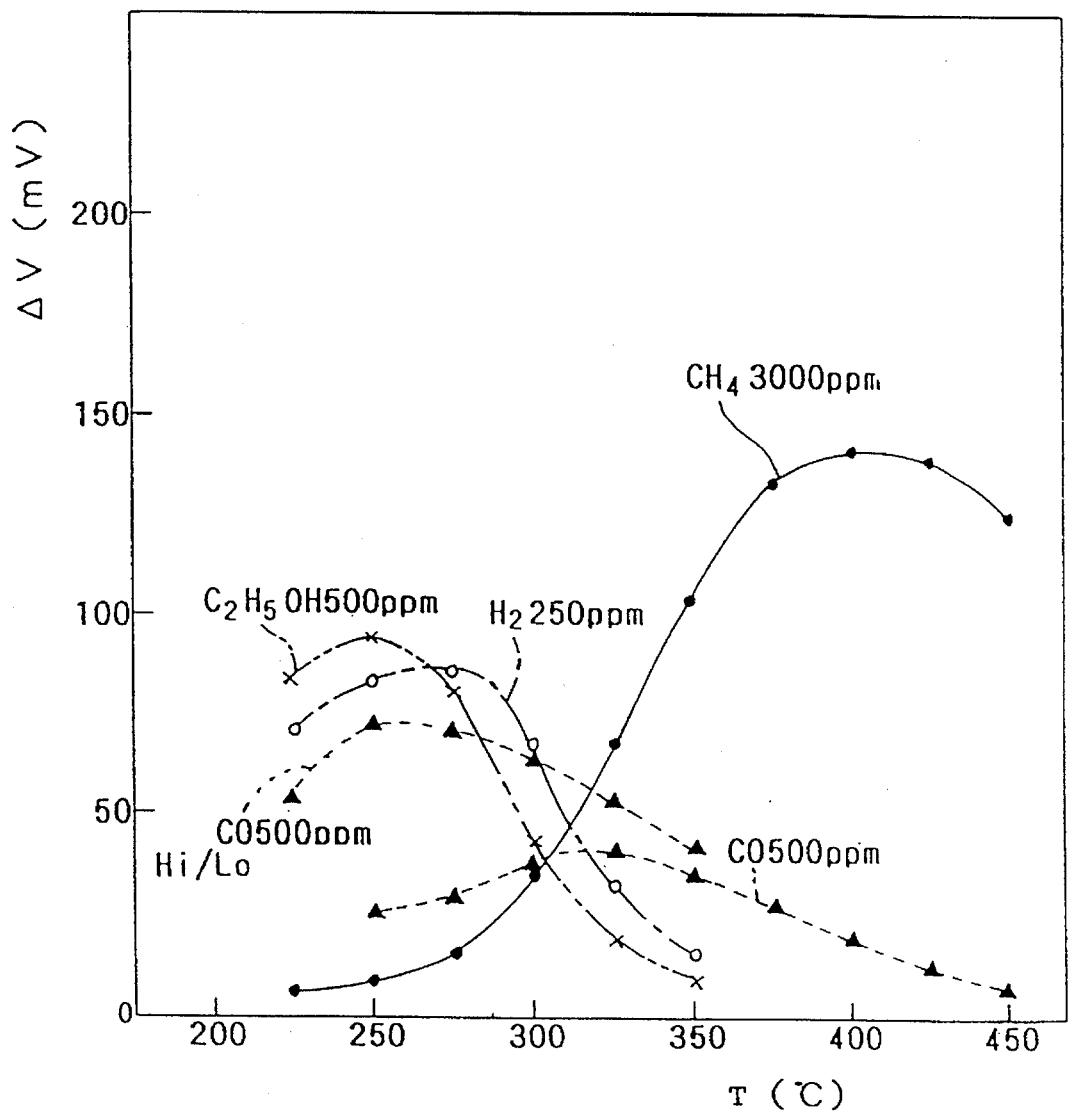
FIG. 5 is a graph showing overall sensitivity characteristics of the sensor.
Figure 6:
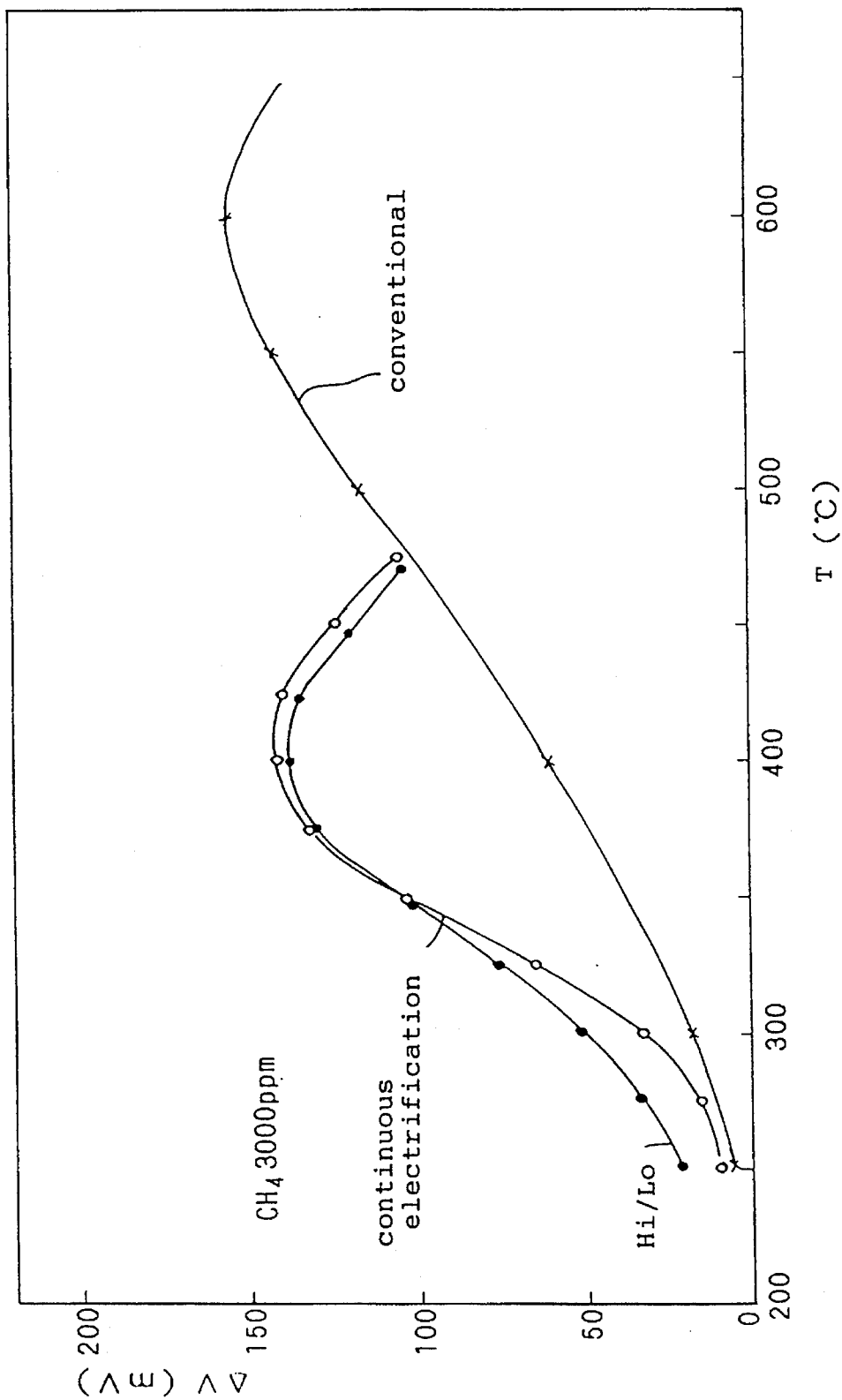
FIG. 6 is a graph for comparing sensitivity characteristics with respect to methane of a conventional sensor and the sensor according to the present invention.
Figure 7:
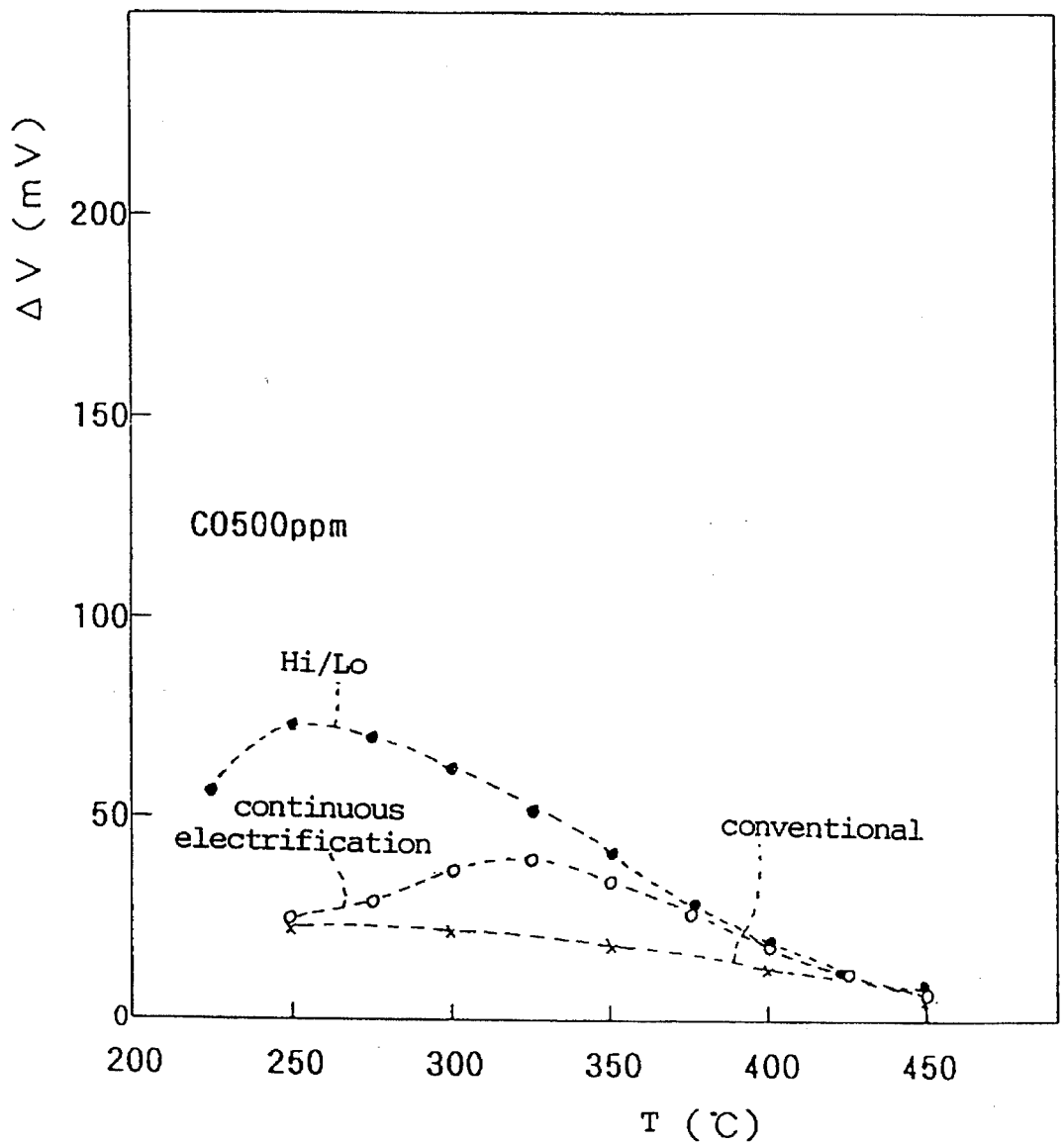
FIG. 7 is a graph for comparing sensitivity characteristics with respect to carbon monoxide of the conventional sensor and the sensor according to the present invention.
Figure 8:
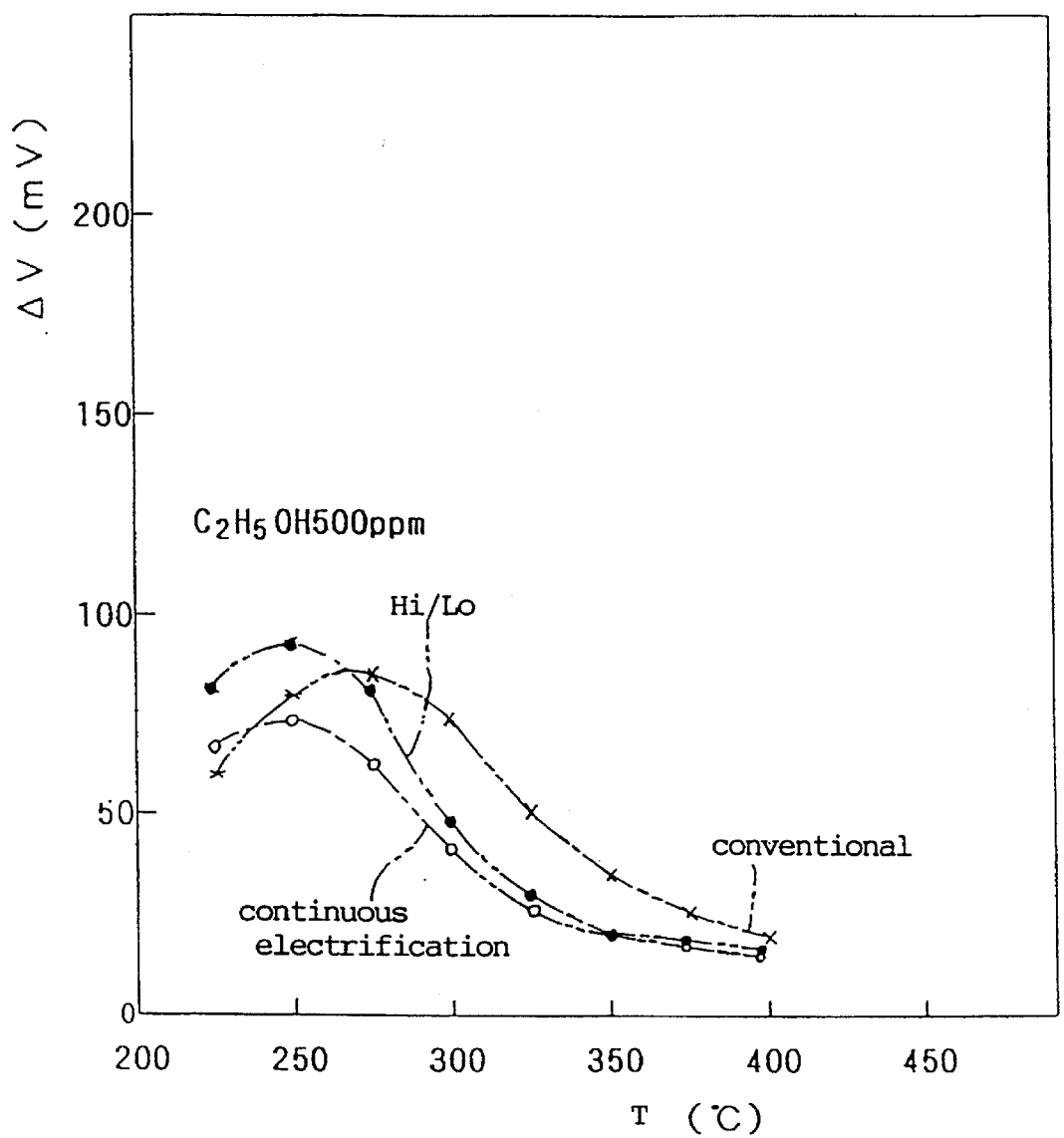
FIG. 8 is a graph for comparing sensitivity characteristics with respect to alcohol of the conventional sensor and the sensor according to the present invention.

Operating conditions of the gas detecting apparatus and sensitivity characteristics of the sensor according to the present invention will be described with reference to FIGS. 3 through 5. FIG. 3 shows sensitivity characteristics of the sensor with the sensitive section 2 maintained at the incomplete combustion gas detecting temperature to detect the incomplete combustion gas. FIG. 4 shows sensitivity characteristics of the sensor with the sensitive section 2 maintained at the fuel gas detecting temperature to detect the fuel gas. FIG. 5 shows sensitivity characteristics of the sensor for an overall temperature range including the above detecting temperatures, which is set to the gas detecting apparatus according to the present invention. In each of these figures, the horizontal axis represents surface temperatures of the sensor, while the vertical axis represents sensor outputs. In each figure, the gases detected are methane (indicated by round black dots), carbon monoxide (black triangles on a broken line), hydrogen (circles on a dot-and-dash line) and alcohol (crosses on a two-dots-and-dash line).

Gas concentrations are different in FIGS. 3 and 4 showing sensitivity characteristics of the sensor when detecting the incomplete combustion gas and fuel gas, respectively. On the other hand, FIG. 5 shows mainly sensitivity characteristics of the sensor within an operating temperature range.

The respective detecting states will be described below:

(1) Incomplete Combustion Detecting State:

In the incomplete combustion detecting state for which sensitivity characteristics are shown in FIG. 3, the gas detected mainly is carbon monoxide. At this time, the temperature of sensitive section 2 is set to 300° C. for carrying out the detection. In this state, it is therefore an important consideration that selectivity for carbon monoxide is secured with respect to a relatively low concentration of methane and to other gases (particularly alcohol). As seen from FIG. 3, in the gas detecting apparatus according to the present invention, good selectivity is secured with respect to methane and some selectivity with respect to alcohol at the incomplete combustion gas detecting temperature. Regarding hydrogen, incomplete combustion produces hydrogen in about half the concentration of carbon monoxide, and it may therefore be considered that both carbon monoxide and hydrogen are detected to determine an incomplete combustion.

(2) Fuel Gas Detecting State:

In the fuel gas detecting state for which sensitivity characteristics are shown in FIG. 4, the gas detected mainly is methane. At this time, the temperature of sensitive section 2 is set to 450° C. for carrying out the detection. In this case, it is necessary to secure selectivity with respect to relatively high concentrations of carbon monoxide, hydrogen, alcohol and the like. As seen from FIG. 4, in the sensor according to the present invention, good selectivity is secured with respect to carbon monoxide, hydrogen and alcohol at the fuel gas detecting temperature.

(3) Detecting Temperature Selection:

FIG. 5 shows sensitivity characteristics for the respective gases in an overall detecting temperature range (200° to 450° C.) of the gas detecting apparatus according to the present invention. However, for carbon monoxide, FIG. 5 includes characteristics occurring in a continuous state of electrification where the sensor is maintained at a fixed temperature, and those occurring with temperature switching. As seen from the illustrated characteristics, a region of maximum sensitivity to carbon monoxide, hydrogen and alcohol exists around 250° to 280° C., and a region of maximum sensitivity to methane around 400° C. The gas detection according to the present invention is carded out for the respective gases in temperature ranges higher than peak positions showing maximum sensitivity. Such selection of detecting temperatures provides the following advantages in relation to carbon monoxide and methane:

(4) Regarding Carbon Monoxide:

Compared with the gentle sensitivity curves of carbon monoxide, the sensitivity to alcohol falls sharply in a high temperature range above 270° C. In order to increase selectivity for alcohol, the detecting temperature may be set higher than the carbon monoxide peak.

(5) Regarding Methane:

The point of maximum sensitivity to methane is around 400° C. To increase selectivity with respect to high concentration gases (e.g. hydrogen, carbon monoxide and spray), methane may be detected at a higher temperature of 450° C. to distinguish from the interfering gases.

Other embodiments will be described hereinafter.

(a) In the above embodiment, ceria is used as an example of substances mixed into the oxide semiconductor. Silicon oxide ($SiO_2$), titanium oxide ($TiO_2$) and zirconium oxide ($ZrO_2$) produce substantially the same effect as ceria. Thus, these substances are collectively called herein an inactive to gas combustion, heat resistant, quadrivalent metallic oxide ($MO_2$ in which M is a quadrivalent metal).

Table 1 shows measurements of temperature and sensitivity showing maximum sensitivity to carbon monoxide (CO) where each of the above substances is mixed in the ratio $MO_2/SnO_2=0.1$ mol %. The concentration of carbon monoxide here is 500 ppm.

It will be seen from these results that the temperature ranges of maximum sensitivity based on employment of these substances are little different from the case of ceria, and therefore that these substances are feasible in regard of sensitivity also. Here, the sensitivity to alcohol and methane acting as interfering gases is about 40 mV or below.

The temperatures showing maximum sensitivity in methane detection are nearly the same for the four oxides (the high temperature apparently being determined by $SnO_2$ activity), providing situations similar to the foregoing embodiment regarding fuel gas detection.

TABLE 1

| substances | temp. of max. sensitivity to CO gas (°C.) | CO gas sensitivity (mV) |
| --- | --- | --- |
| $CeO_2$ | 250 | 72 |
| $SiO_2$ | 280 | 50 |
| $TiO_2$ | 260 | 56 |
| $ZrO_2$ | 265 | 62 |

Figure 9A:
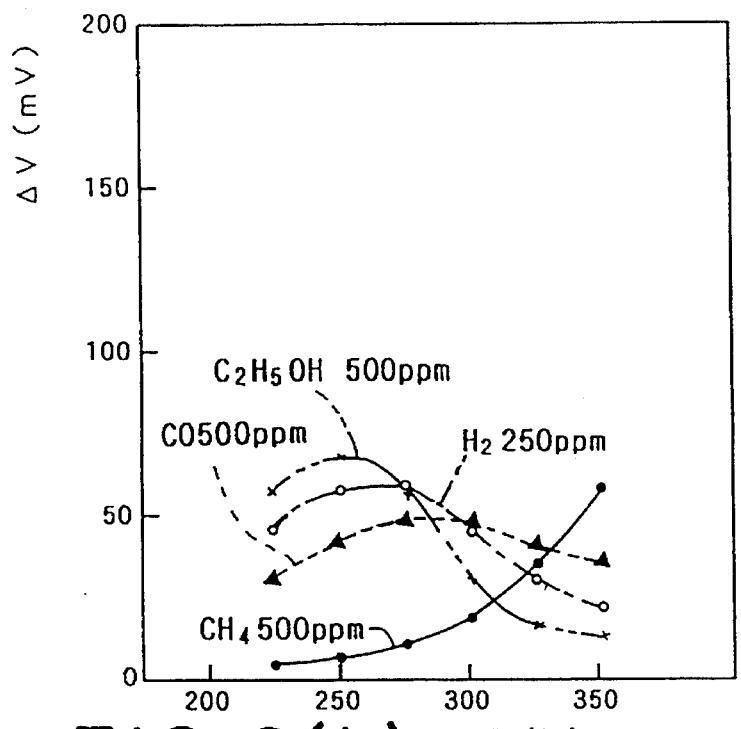
FIG. 9(a) and FIG. 9(b) are graphs corresponding to FIGS. 3 and 4 and showing sensitivity characteristics of a sensor having silicon oxide.
Figure 9B:
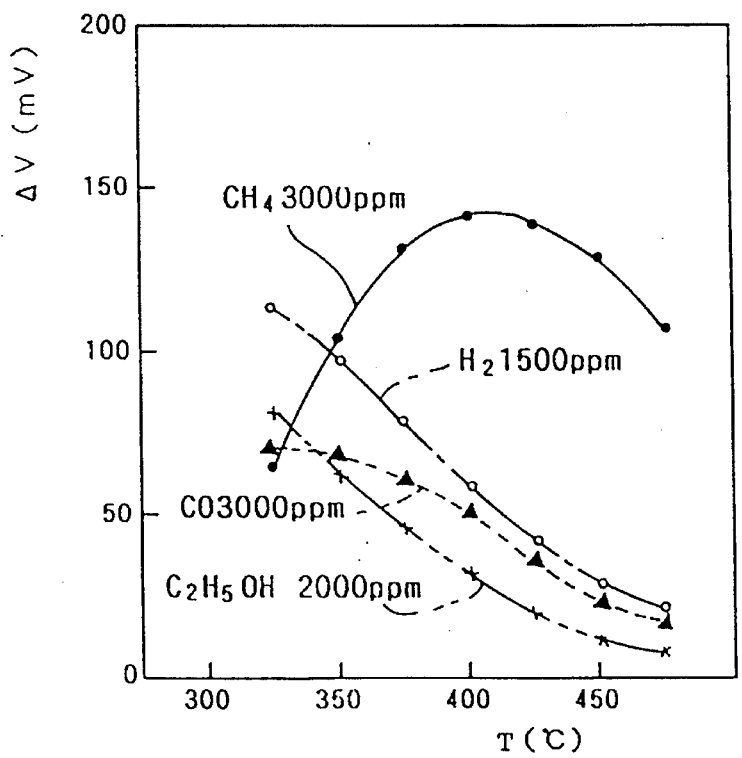
Figure 10A:
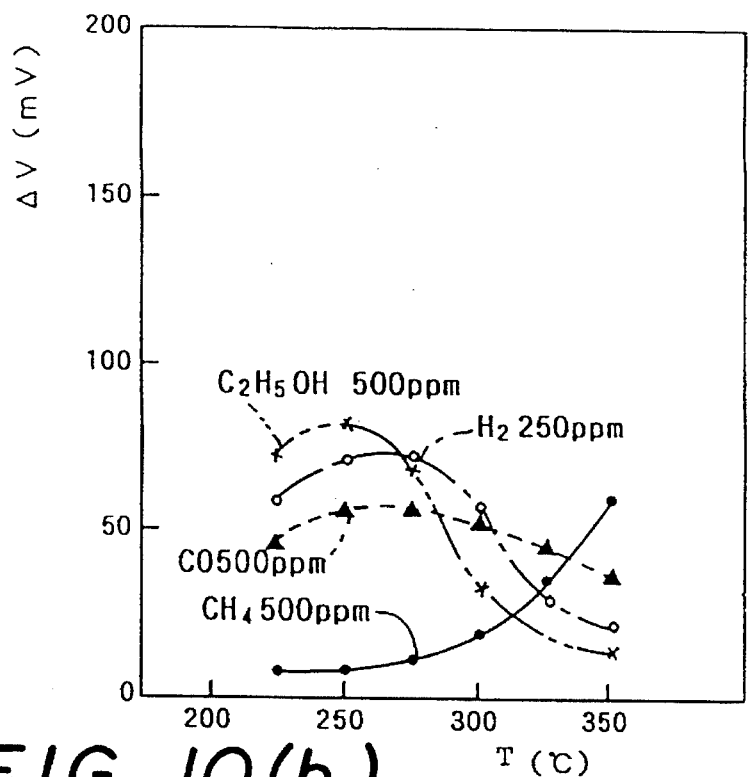
FIG. 10(a) and FIG. 10(b) are graphs corresponding to FIGS. 3 and 4 and showing sensitivity characteristics of a sensor having titanium oxide.
Figure 10B:
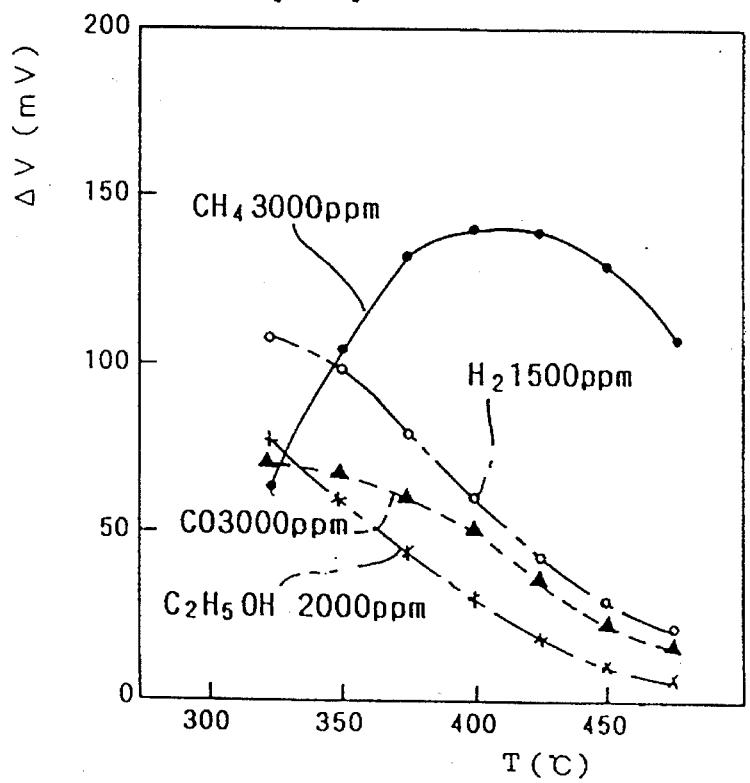
Figure 11:
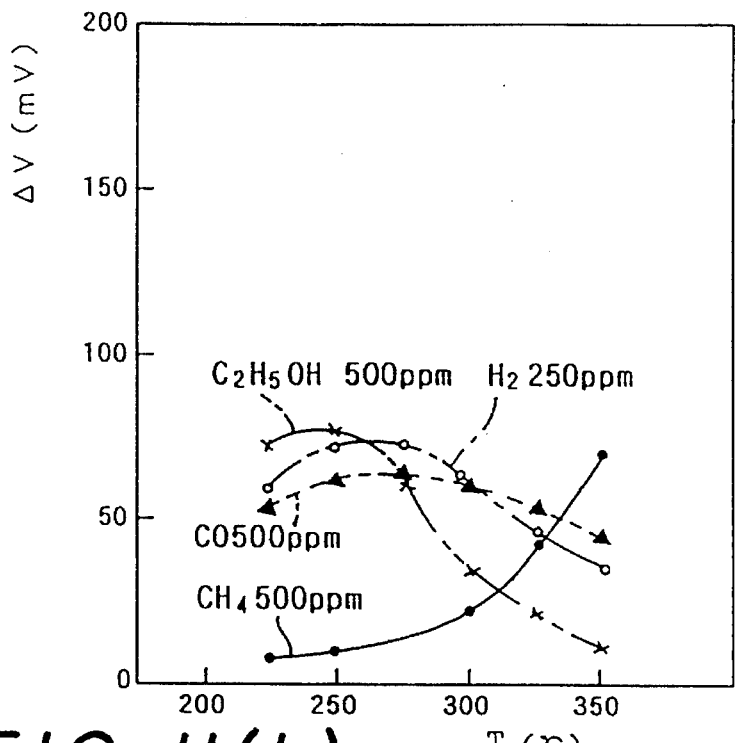
FIG. 11(a) and FIG. 11(b) are graphs corresponding to FIGS. 3 and 4 and showing sensitivity characteristics of a sensor having zirconium oxide.
Figure 11:
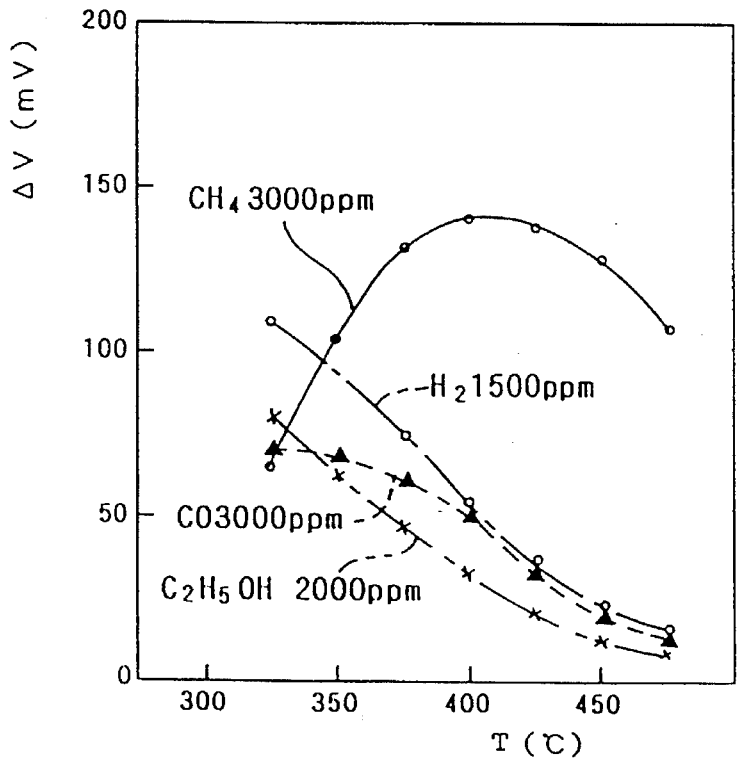

FIGS. 9 through 11 show sensitivity characteristics of sensors corresponding to FIGS. 3 and 4, where the metallic oxides other than ceria are used. FIG. 9 shows a case where silicon oxide ($SiO_2$) is mixed in 0.12 mol %. FIG. 10 shows a case where titanium oxide ($TiO_2$) is mixed in 0.14 mol %. Finally, FIG. 11 shows a case where zirconium oxide ($ZrO_2$) is mixed in 0.12 mol %. In the respective figures, (a) shows sensitivity characteristics of the sensor with the sensitive section 2 maintained at the incomplete combustion gas detecting temperature to detect the incomplete combustion gas, and (b) shows sensitivity characteristics of the sensor with the sensitive section 2 maintained at the fuel gas detecting temperature to detect the fuel gas. In these figures, as in FIGS. 3 and 4, the horizontal axis represents surface temperatures of the sensor, while the vertical axis represents sensor outputs. In each figure, the gases detected are methane (indicated by round black dots), carbon monoxide (black triangles on a broken line), hydrogen (circles on a dot-and-dash line) and alcohol (crosses on a two-dots-and-dash line).

It will be seen from these results that, with the respective metallic oxides employed, the respective gases may be selectively detected in the two detection states.

(b) As described in the foregoing embodiment, the sensor of the present invention itself has a selectivity for alcohol. An activated carbon filter may be disposed in an area of gas passage leading to the sensitive section. This provides the effect of avoiding a false alarm due to a high concentration (in the order of 2,000 ppm) of alcohol produced by cooking.

(c) In the foregoing embodiment, cycles of alternate switching between the fuel gas detecting temperature and incomplete combustion gas detecting temperature are based on unit time (10 seconds in the embodiment). Instead, the sensor may normally be maintained in the fuel gas detecting state. In this case, the fuel gas detecting state at the higher detecting temperature is maintained longer than the incomplete combustion detecting state at the lower detecting temperature (e.g. the detection at the lower temperature for 3 seconds, and the detection at the higher temperature for 27 seconds). Such switching provides the advantage of increased long-term stability. Further, the detecting temperatures may be switched in any other way.

(d) Apart from the foregoing embodiments, the sensor according to the present invention was used to detect LP gas. Similar results were obtained though not a selectivity comparable to one for methane.

What is claimed is:

1. A gas detecting method, comprising the steps of:

providing a low heat capacity, hot-wire semiconductor type gas sensor having a sensitive section comprising an oxide semiconductor formed mainly of valency-controlled tin oxide ($SnO_2$), the oxide semiconductor including an inhibitor to inhibit the combustion of the carbon monoxide, the inhibitor comprising an incombustible, heat resistant, quadrivalent metallic oxide; a dense sintered layer formed on a surface of the sensitive section, the dense sintered layer comprising a tin oxide, the tin oxide forming the dense sintered layer having a larger specific surface area than the tin oxide for forming the sensitive section; and the gas sensor including a coil resistor mounted in the sensitive section;

alternately switching the temperature of a sensitive section between a fuel gas detecting temperature for detecting a fuel gas having methane as a main component thereof and an incomplete combustion gas detecting temperature for detecting an incomplete combustion gas having carbon monoxide as a main component thereof;

detecting a fuel gas having methane as a main component thereof at said fuel gas detecting temperature; and detecting an incomplete combustion gas having carbon monoxide as a main component thereof at said incomplete combustion gas detecting temperature.

2. A gas detecting method as defined in claim 1, further comprising the steps of: providing the sensitive section with an outside diameter of 1 mm at most; forming said incombustible, heat resistant, quadrivalent metallic oxide as a single metallic oxide selected from the group consisting of ceria ($CeO_2$), silicon oxide ($SiO_2$), titanium oxide ($TiO_2$) and zirconium oxide ($ZrO_2$); mixing said metallic oxide in a ratio of 0.01 to 0.5 mol % with respect to said tin oxide; and forming said dense sintered layer in a thickness of 1 to 20 μm on a surface of said sensitive section by sintering tin oxide having a specific surface area of 50 to 150 $m^2/g$.

3. A gas detecting method as defined in claim 2, wherein said fuel gas detecting temperature is around 450° C., and said incomplete combustion gas detecting temperature is around 300° C., said method further comprising the step of: alternately switching the sensitive section between said fuel gas detecting temperature and said incomplete combustion gas detecting temperature every unit of time.

4. A gas detecting apparatus, comprising:

a gas sensor including:
 a sensitive section comprising an oxide semiconductor formed mainly of valency-controlled tin oxide, said oxide semiconductor including an inhibitor to inhibit the combustion of the carbon monoxide, said inhibitor comprising an incombustible, heat resistant, quadrivalent metallic oxide,
 a dense sintered layer formed on a surface of said sensitive section, said dense sintered layer comprising a tin oxide, said tin oxide forming said dense sintered layer having a larger specific surface area than the tin oxide for forming said sensitive section, and
 a coil resistor mounted in said sensitive section; and switching means for alternately switching the temperature of said sensitive section between a fuel gas detecting temperature for detecting a fuel gas having methane as a main component thereof and an incomplete combustion gas detecting temperature for detecting an incomplete combustion gas having carbon monoxide as a main component thereof.

5. A gas detecting apparatus as defined in claim 4, wherein said switching means comprises applied voltage switching means for switching voltages applied to said hot-wire semiconductor type gas sensor.

6. A gas detecting apparatus as defined in claim 4, wherein said sensitive section has an outside diameter of 1 mm at most, said incombustible, heat resistant, quadrivalent metallic oxide is a single metallic oxide selected from the group consisting of ceria ($CeO_2$), silicon oxide ($SiO_2$), titanium oxide ($TiO_2$) and zirconium oxide ($ZrO_2$), said metallic oxide being mixed in a ratio of 0.01 to 0.5 mol % with respect to said tin oxide, and said dense sintered layer being formed in a thickness of 1 to 20 μm on a surface of said sensitive section by sintering tin oxide having a specific surface area of 50 t 150 $m^2/g$.

7. A gas detecting apparatus as defined in claim 6, wherein said fuel gas detecting temperature is around 450° C., and said incomplete combustion gas detecting temperature is around 300° C., said switching means effecting alternate switching between said fuel gas detecting temperature and said incomplete combustion gas detecting temperature every unit of time.

8. A gas detecting apparatus as defined in claim 6, wherein said metallic oxide is mixed in a ratio of 0.03 to 0.3 mol % with respect to said tin oxide.

9. A gas detecting apparatus as defined in claim 7, further comprising an activated carbon filter disposed in an area of gas passage leading to said sensitive section.

10. A gas detecting apparatus as defined in claim 7, further comprising alarm generating means for giving an alarm upon detection of one of said fuel gas and said incomplete combustion gas.

11. A gas detecting apparatus comprising:

a gas sensor including:
 a sensitive section comprising an oxide semiconductor formed mainly of valency-controlled tin oxide, said oxide semiconductor including an inhibitor to inhibit the combustion of the carbon monoxide, said inhibitor comprising an incombustible, heat resistant, quadrivalent metallic oxide selected from the group consisting of ceria ($CeO_2$), silicon oxide ($SiO_2$), titanium oxide ($TiO_2$) and zirconium oxide ($ZrO_2$),
 a dense sintered layer formed on a surface of said sensitive section, said dense sintered layer comprising a tin oxide, said tin oxide forming said dense sintered layer having a larger specific surface area than the tin oxide for forming said sensitive section, and
 a coil resistor mounted in said sensitive section; and switching means for alternately switching the temperature of said sensitive section between a fuel gas detecting temperature for detecting a fuel gas having methane as a main component thereof and an incomplete combustion gas detecting temperature for detecting an incomplete combustion gas having carbon monoxide as a main component thereof.

* * * * *